United States Patent [19]

LeClerc et al.

[11] Patent Number: 4,952,573

[45] Date of Patent: Aug. 28, 1990

[54] COMPOUNDS HAVING GABA LIKE ACTIVITY, AND USE OF SAME IN TISSUE IRRIGATING SOLUTIONS

[75] Inventors: Gerard LeClerc; Beatrice Ruhland; Guy Andermann, all of Strasburg; Georges de Burlet, Beblenheim; Michel Dietz, Barr, all of France

[73] Assignee: Laboratoirs Alcon S.A., Toulouse, France

[21] Appl. No.: 172,047

[22] Filed: Mar. 23, 1988

[51] Int. Cl.$^5$ .................. C07D 215/48; A61K 31/47
[52] U.S. Cl. ..................................... 514/311; 546/164; 546/165
[58] Field of Search ................. 546/165, 164; 514/311

[56] References Cited

U.S. PATENT DOCUMENTS

| | | | |
|---|---|---|---|
| 3,975,530 | 8/1976 | Durant et al. | 514/378 |
| 4,375,472 | 3/1983 | Durant et al. | 514/378 |
| 4,443,432 | 4/1984 | Garabedian et al. | 424/127 |
| 4,550,022 | 10/1985 | Garabedian et al. | 424/127 |

FOREIGN PATENT DOCUMENTS 139412 4/1930 Switzerland .

OTHER PUBLICATIONS

Dikstein et al, *Corneal Endothelial Pumping in the Presence of Insulin and GABA;* Exp. Eve Res., vol. 31, pp. 239–241 (1980).
The Merch Index, pp. 746, 1342, 1343.

*Primary Examiner*—David B. Springer
*Attorney, Agent, or Firm*—James A. Arno; Gregg C. Brown; Sally S. Yeager

[57] ABSTRACT

Compounds which enhance the efficiency of the corneal endothelial fluid pump thereby promoting normal corneal function and deturgescence of swollen corneas, and methods for the compounds' synthesis are described. In addition, surgical irrigating solutions which include one or more of the compounds are discussed along with methods for their use.

15 Claims, 1 Drawing Sheet

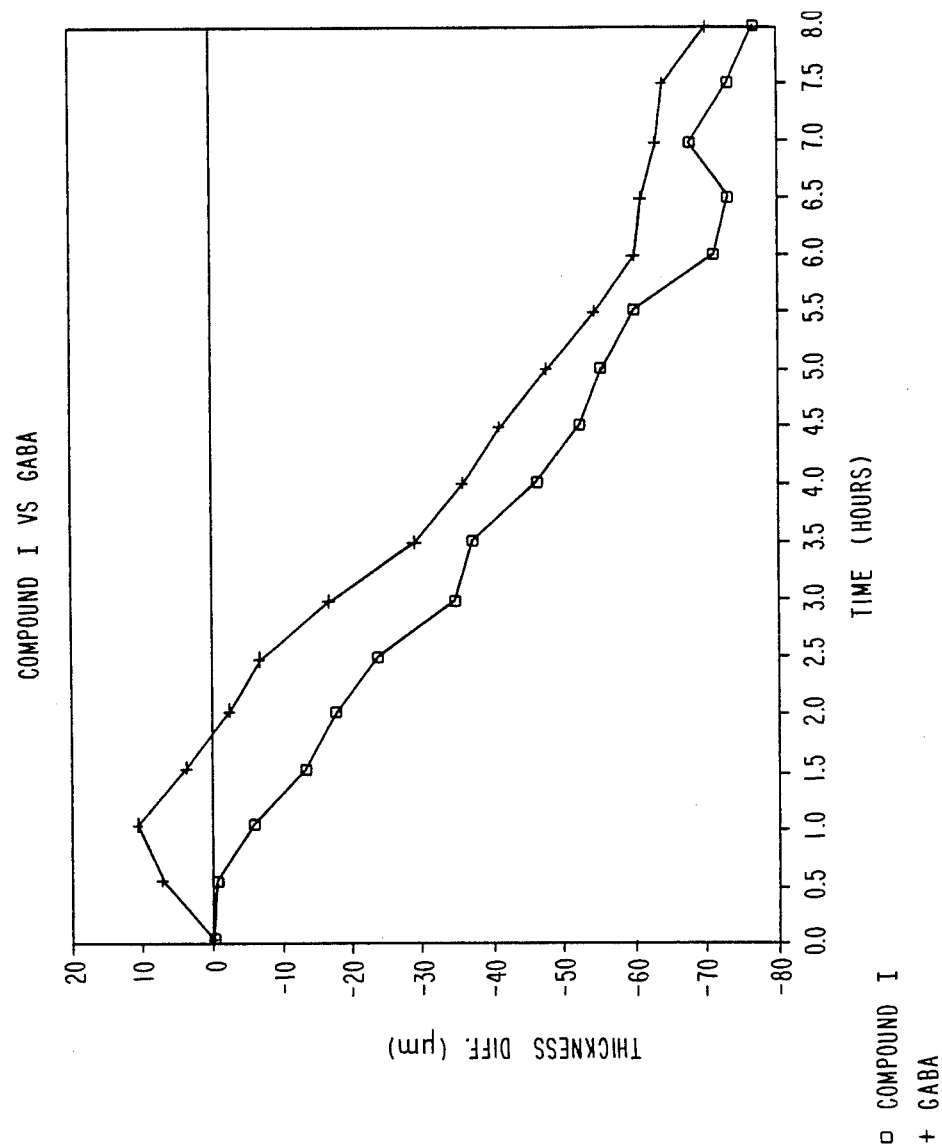

COMPOUNDS HAVING GABA LIKE ACTIVITY, AND USE OF SAME IN TISSUE IRRIGATING SOLUTIONS

FIELD OF THE INVENTION

The present invention relates to certain new and useful compounds which have been found to have GABA like activity, and to methods of synthesizing those compounds. The present invention further relates to irrigating solutions for use within the human body and more particularly to solutions useful for irrigating tissues during surgery, such as ophthalmic, neural, cardiovascular or otic surgery. More particularly, this invention relates to ophthalmic irrigating solutions which comprise, in addition to conventional components, one or more compounds having GABA like activity.

BACKGROUND OF THE INVENTION

Any scission into the body is detrimental and invariably results in cell loss. The need to keep cell loss to a minimum is particularly crucial during any surgical procedure performed on delicate and irreplaceable tissues, for example, ophthalmic or nerve tissue.

The cornea of the eye is comprised of five layers: epithelium, Bowman's membrane, stroma, Decemet's membrane, and endothelium. The endothelium layer is particularly vulnerable to trauma, and protection of the endothelium is particularly important because endothelial cells are infrequently, if ever, replaced as a normal process in adult life. The corneal endothelium is principally responsible for maintaining proper hydration of the stromal layer. The stromal layer has a tendency to imbibe fluid, a tendency which is counterbalanced by outward fluid transport via the endothelium. If the proper fluid balance is not maintained in the stromal layer, the cornea thickens and the characteristic transparency of the cornea is lost. Failure of the endothelium to perform its fluid transport function for even short periods of time will result in corneal thickening and visual clouding. In addition, cell loss or damage in the endothelial layer results in decreased vision. Because of the importance and vulnerability of the endothelial layer, it is necessary during eye surgery, such as cataract and retinal surgery or corneal transplants, to make provisions for the protection of the endothelial cells.

A significant factor causing cell loss during tissue scission is the traumatic change in environment experienced by the cells. Exposure to the atmosphere presents a far different environment for internal cells than is provided by the natural fluids in which they are bathed. To simulate the natural cellular environment during surgery thereby preventing cell damage, exposed tissue is frequently irrigated in solutions which attempt to approximate the chemical composition and/or physical properties of natural body fluids. The value of bathing ophthalmic tissue during surgery to prevent cell damage has long been recognized. For internal ocular tissues, such as the endothelium, the aqueous humor is the natural bathing fluid. Therefore, an ideal ophthalmic irrigating solution should simulate or surpass the cell preservation properties of the aqueous humor.

Of primary concern for any tissue irrigating solution is that the osmolality of the solution be generally isotonic relative to cellular fluids, so as to maintain equal osmotic pressure within and without the cell membranes. To this end, one of the early ophthalmic irrigating solutions was isotonic (0.9%) saline. However, it has long been recognized that isotonic saline is quite inadequate as an ophthalmic irrigating solution because its use has been shown to result in endothelial cell swelling, cell damage, and consequent corneal clouding.

Because of the inadequacy of isotonic saline, various alternative electrolyte solutions have been proposed as irrigating solutions, particularly ophthalmic irrigating solutions which more closely resemble the aqueous humor and prevent cell damage and corneal clouding. Standard electrolyte solutions primarily intended for intravenous injection, such as Ringer's solution and lactated Ringer's solution, have been used as ophthalmic irrigating solutions because they are readily available and are sterile.

An electrolyte solution specifically intended for ophthalmic irrigation is available from Alcon Laboratories, Inc. as BSS ®. That solution, which may be characterized as being a balanced salt solution, contains the essential ions calcium, sodium, potassium, magnesium and chloride in generally optimal concentrations for ocular tissue, and has an acetate-citrate buffer system which is compatible with divalent calcium and magnesium ions.

Electrolyte solutions used for ophthalmic irrigation, such as lactated Ringer's solution and balanced salt solutions, represent improvements over normal saline because they provide necessary ions in addition to the sodium and chloride ions provided by isotonic saline. For example, magnesium is an important cofactor for adenosine triphosphotase, an enzyme which plays an important role in mediating the fluid transport pump in the eye. Calcium is necessary to maintain the endothelial junction, and potassium is an important factor in many biochemical processes. Moreover, the fluid transport pump of the endothelium requires a proper sodium, potassium ion ratio (Na+/K+) to function. Due to these additions the previously known electrolyte solutions used to irrigate ocular tissue have reduced, but not eliminated, corneal swelling and cell damage during surgery.

The need for improved ophthalmic irrigating solutions continues, particularly in view of new surgical techniques which may probe deeper into the eye requiring several hours of operating time. For example, surgical advances now permit surgery in the vitreous (posterior) chamber to remove opacified vitreous humor or to repair retinal detachment. Such operations can require up to three hours. Inner cells chances of damage increase the longer they are exposed, but improved irrigating solutions can help prevent damage resulting from exposure during lengthy procedures.

During eye surgery and particularly during surgery which requires extended periods of time, proper electrolytic balance alone is insufficient to protect the corneal endothelium. To prevent cell damage and maintain proper corneal thickness, an irrigating solution, in addition to maintaining electrolytic balance, must also provide metabolic support and must particularly provide factors needed for the enzyme-mediated sodium/potassium ion pump system through which excess fluid is removed from the stroma.

Factors determined to be necessary for sustained metabolism of endothelial cells include dextrose, glutathione and bicarbonate. All have been shown to be important in maintaining the structural integrity of endothelial cells. Dextrose provides a substrate for various metabolic pathways and glutathione has been shown to aid the adenosine-triphosphotase mediated metabolic pump by maintaining the proper sodium, potassium ion ratio. In addition, bicarbonate is useful in maintaining proper pH of the irrigating solution.

Glutathione bicarbonate-Ringer's solution (GBR) has incorporated the above-mentioned factors and is effective in maintaining corneal thickness and endothelial cell integrity for up to three hours. However, its use has been limited for reasons of sterility and stability.

U.S. Pat. Nos. 4,443,432 and 4,550,022 (Garabedian et al.) assigned to Alcon Laboratories, Inc. describe tissue irrigating compositions which comprise a balanced salt solution in combination with sodium bicarbonate, dextrose and glutathione. The entire contents of these two patents are hereby incorporated by reference in the present specification.

The role of gamma-aminobutyric acid (GABA) in stimulating the corneal endothelial fluid pump has been previously recognized. More particularly, prior studies have indicated that GABA enhances the pumping efficiency of the corneal endothelial fluid pump thereby promoting normal corneal function and preventing or minimizing corneal swelling. According to one study, the activity of GABA in this regard is comparable to or better than that of oxidized glutathione. See Dikstein et al., Experimental Eye Research, Vol. 31, pages 239–241 (1980).

A principal objective of the present invention is the provision of new compounds having GABA like activity and methods of synthesizing those compounds.

A further objective of the present invention is the provision of ophthalmic surgical irrigating solutions containing one or more compounds having GABA like activity and methods for their use.

SUMMARY OF THE INVENTION

The present invention is directed to provision of a class of new chemical compounds which have been found to have GABA like activity, and to the use of those compounds in surgical irrigating solutions, particularly irrigating solutions useful in ophthalmic surgery. For purposes of the present specification, the phrase "GABA like activity" is intended to mean that the compounds have pharmacological activity similar to that of GABA. More particularly, the compounds have been found to promote corneal deswelling, and this deswelling effect is believed to be attributable to enhancement of the pumping efficiency of the corneal endothelial fluid pump. As mentioned above, GABA has been reported to have a similar enhancing effect on the corneal endothelial fluid pump.

The compounds of the present invention will typically be utilized in conjunction with other conventional components, such as a balanced salt solution or a balanced salt solution containing glutathione, such as BSS Plus ®, to provide enhanced irrigation of tissues, particularly irrigation of the corneal endothelium during ophthalmic surgical procedures. The compounds may, however, be utilized in single component formulations specifically designed to reverse or prevent corneal swelling. In a preferred embodiment of the present invention, one or more of the compounds of the present invention is combined with a balanced salt solution, sodium bicarbonate, and dextrose.

The pharmacological properties of irrigating solutions containing one or more of the compounds of the present invention are considered to be superior to those of analogous prior art irrigating solutions. This superiority is believed to be attributable to the positive effect of the compounds of the present invention on the corneal endothelial fluid pump.

BRIEF DESCRIPTION OF THE DRAWING

The sole FIGURE of drawing is a graph illustrating the corneal deswelling activity of one of the compounds of the present invention.

DETAILED DESCRIPTION OF THE INVENTION

The compounds of the present invention are derivatives of isonipecotic acid and 4,5,6,7-tetrahydroisoxazolo[5,4-c]pyridin-3-ol (THIP). Both isonipecotic acid and THIP are known compounds. Both are known to have GABA agonist activity. Reference is made to The Merck Index, Tenth Edition, pp. 746 and 1342 (1983) for further information concerning isonipecotic acid and THIP.

The compounds of the present invention have the following structures:

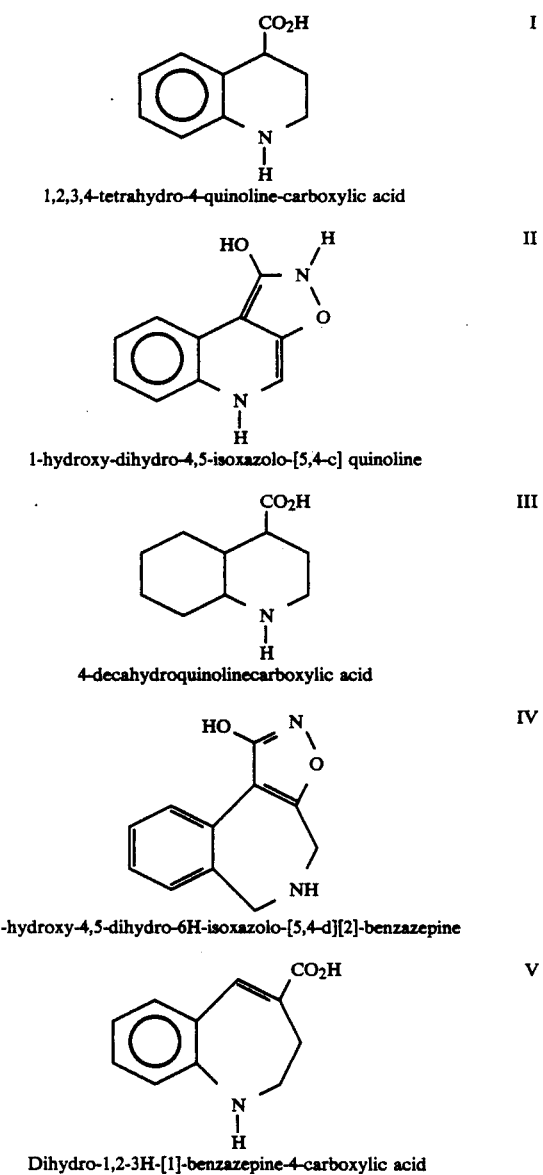

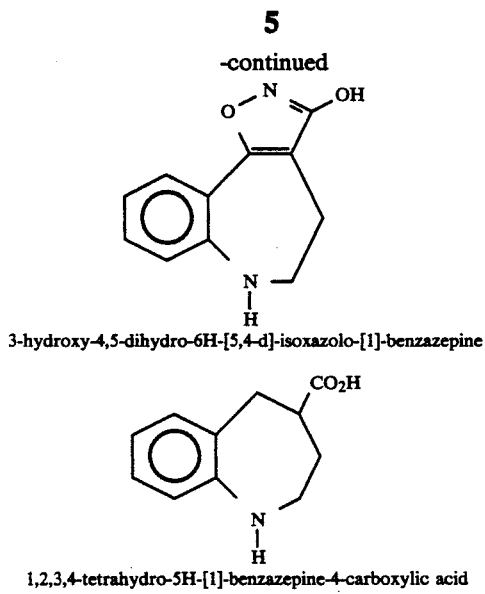

3-hydroxy-4,5-dihydro-6H-[5,4-d]-isoxazolo-[1]-benzazepine 1,2,3,4-tetrahydro-5H-[1]-benzazepine-4-carboxylic acid Methods for synthesizing the compounds of the present invention are described in the following examples.

EXAMPLE 1

(Synthesis of Compound I)

Compound I was prepared according to the following scheme:

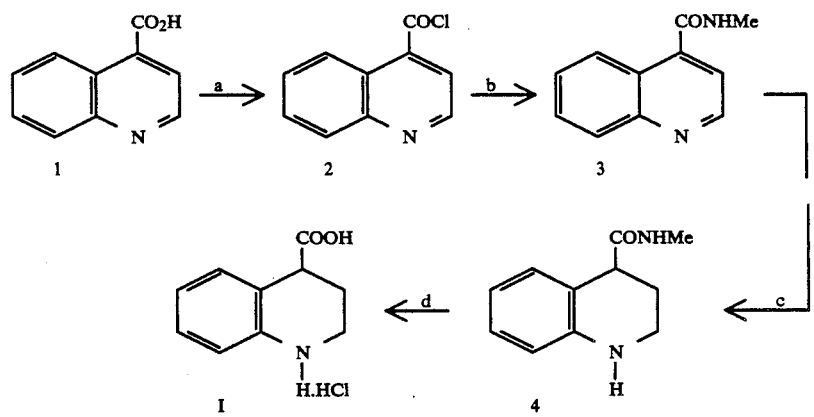

a = SOCl$_2$; b = MeNMe/NaO; c = NiAl/MeOH/KOH; d = HCl 6N;

The preparation of compound I involved, as a key step, the reduction of 4-quinolinecarboxylic acid 1 to the corresponding 1, 2, 3, 4- tetrahydro-4-quinolinecarboxylic acid. The 4 quinolinecarboxamide 3 was prepared from the acid chloride HCl salt 2 by means of known procedures, see E. Spath, H. Spitzer, Ber 59B 1477 (1926) by Schotten-Baumann procedure, see Vogel, AI, Ed. "Practical Organic Chemistry"; Longmans: London, 582 (1967). The quinoline 3 was reduced over Nickel-Aluminium alloy in potassium hydroxyde solution according to a recently described method, see G. Lunn, E. B. Sonsone, J. Org. Chem. 51, 513–517 (1986). The carboxamide 4 was hydrolyzed to give compound I.

EXPERIMENTAL SECTION

Preparation of N-Methyl-1, 2, 3, 4-tetrahydro-4 quinolinecarboxamide (4).

The procedure of G. Lunn was followed. 1.5 g (8 mmoles) of 3 were dissolved in methanol (20 ml) and potassium hydroxide solution (1M, 20 ml) was added. This mixture was stirred and Nickel-Aluminium alloy (3,5 g) was added in portions over 1 hour. After stirring for a further 1½ hours the mixture was filtered through a pad of celite and washed through with dichloromethane. The aqueous layer was extracted 3 times with the organic layer and the extracts were dried over MgSO4 and evaporated. The crude residue was chromatographed on a silica gel column and eluted with EtOAc/Et$_3$N (95/5) to give 1.04 g (68%) of 4 as a yellow powder, mp 107° C.; $^1$H NMR 200 MHz (MeOD) δ=1.88–2.04 (1H, m) 2.13–2.27 (1H, m) 2.74 (3H, s) 3.21–3.31 (2H, m) 3.61 (1H, t, J=6.25Hz) 6.52–6.60 (2H, m) 6.87–7.01 (2H, m). IR CONHMe=1650 cm$^{1-}$.

Preparation of 1, 2, 3, 4-tetrahydro-4-quinolinecarboxylic acid, compound I.

A solution of 4 (1.6 g, 8.4 mmoles) in a solution of hydrochloric acid (60 ml, 6M) was refluxed for 14 hours. After evaporation to dryness in vacuo, the residue was treated with a solution of sodium hydroxide (40 ml, 1N). The mixture was extracted with three 40 ml portions of ethyl acetate, the combined and dried (MgSO4) organic phases were evaporated in vacuo. The residue was treated with a solution of hydrochloric acid (50 ml, 6N), and evaporated. The crude product was taken in isopropanol and filtered. Evaporation in vacuo followed by recrystallization (acetonitrile, methanol) of the residue gave compound I (800 mg, 45%) as colorless crystals, mp 154° C. (Found: C 56.34; H 5.77; N 6.80. Calc. for C$_{10}$H$_{12}$ClNO$_2$: C 56.21; H 5.66; N 6.56. Mass spectrum, m/z=177 (M+). $^1$H NMR 200 MHz (MeOD) δ=2.29–2.56 (2H, m) 3.53–3.76 (2H, m) 4.04 (1H, t, J=6.25Hz) 7.31–7.38 (1H, m) 7.43–7.52 (1H, m) 7.58–7.63 (1H, m).

EXAMPLE 2

(Synthesis of Compound II)

Compound II was prepared according to the following scheme:

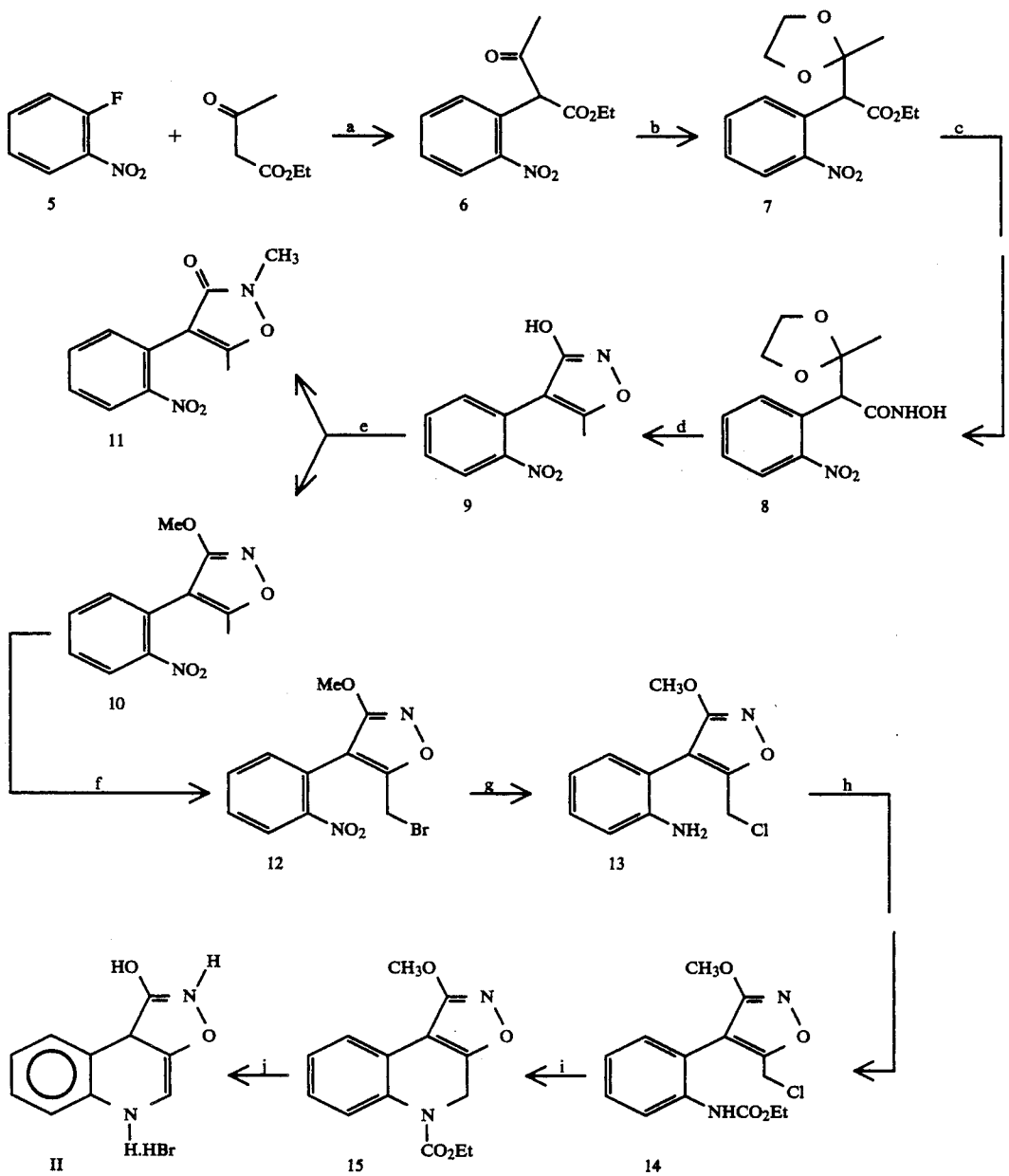

a = NaH/N-methylpyrolidone;
b = glycol/TsOH/toluene;
c = NH$_2$OH, HCl/MeOH/KOH;
d = HCl 12N;
e = CH$_2$N$_2$;
f = NBS/AIBN;
g = SnCl$_2$/HCl;
h = ClCO$_2$Et;
i = K$_2$CO$_3$/Acetone;
j = HBr/AcOH The key step in the reaction sequence is the synthesis of the 3-hydroxy-isoxazole 9 which is accomplished utilizing a reaction sequence analogous to that described by Jacquier, R., Petrus, C., Petrus, F. and Verducci, J. Bull. Soc. Chem. Fr. 1978 (1970). The hydroxamic acid 8 was treated with an ethanolic solution of hydrogen chloride to give 9. Treatment of 9 with diazomethane gave almost equal amounts of the N- and O-methylated products in agreement with general findings (see Jacquier). The amine 13, obtained by SnCl$_2$ reduction of 12, prepared from 10, was protected and cyclized by K$_2$CO$_3$ in compound 15. Cleavage of 15 to the corresponding hydrobromide, was accomplished by treatment with 40% solution of hydrogen bromide in glacial acetic acid.

EXPERIMENTAL SECTION

The structure determinations of the new compounds 8 through compound II shown in the scheme are based on ¹H NMR, mass spectroscopic methods and elemental analyses.

Preparation of benzene acetic acid-(α-acetyl ethylene ketal)-2-nitro- ethyl ester (7).

A mixture of (5.5 g: 0.022 mmoles) of 6 made according to the procedure of 5 J. Bourdais, C. Manieu, Comptes Rendus C 263 84-7 (1966), ethylene glycol (6.6 g: 0.1 mole), 4-toluene sulfonic acid (0.3 g) and 150 ml of toluene was refluxed for ca. 40 hours using a Dean-Stark water separator. The solution was washed with aqueous potassium carbonate (200 ml) and water (200 ml). The organic phase was dried (MgSO4) and evaporated in vacuo to give 7 (6 g) as an oil. CC [silica gel: 130 g; eluents:Hexane containing ether (60/40)] afforded 7 (5 g, 77%) as a yellow crystalline and TLC pure substance. An analytical sample was recrystallized (Hexane) to give 7 as colorless crystals, mp 87° C. (Found: C 56.92; H 6.06; N 4.79; Calc. for $C_{14}H_{17}NO_6$: C 56.95; H 5.80; N 4.74: ¹H NMR 60 MHz CDCl3) δ=1.25 (3H, t, J=9 Hz) 1.35 (3H, s) 3.6–4 (4H, m) 4.2 (2H, q, J-9 Hz) 4.95 (1H, s) 7.3–8 (4H, m).

Preparation of benzene acetic hydroxamic acid-2-nitro-alpha acetyl ethylene ketal (8)

To a stirred ice solution of potassium hydroxide (5.7 g, 100 mmoles) in methanol (15 ml) was added hydroxylammonium chloride (5.6 g, 80 mmoles). After stirring at 0° C. for 30 minutes a solution of 7 (6 g, 20 mmoles) in methanol (15 ml) was added, and the mixture was left at 4° C. for 4 days. After addition of glacial acetic acid (12 ml) and filtration, the filtrate was evaporated in vacuo to give a thick mass which was worked up utilizing column chromatography [silica gel: 180 g; eluents:-dichloromethane-ethyl acetate-methanol (50-47-3)]. There was obtained 3.75 g (66%) of 8 in a crystalline state. An analytical sample was recrystallized (ethyl acetate-isopropyl oxyde) to give colorless crystals, mp 161° C. (Found: C 50.82; H 5; N 9.89. Calc. for $C_{12}H_{14}N_2O_6$: C 51.07; H 5; N 9.93). ¹H NMR 60 MHz (MeOD) δ=1 (3H, s) 3.2–3.6 (4H, m) 4.1 (1H, s) 4.4 (2H, exchangeable D20) 7–7.5 (3H, m) 7.8–8 (1H, m).

Preparation of 3-hydroxy-4-(o-nitrophenyl)-5-methyl-isoxazole (9).

To a solution of 8 (1 g, 3.5 mmoles) in methanol (6 ml) was added concentrate hydrochloric acid (6 ml). After heating to 70° C. for 1 hour the solution was evaporated in vacuo. The residue was treated with water (10 ml) and extracted with three 20 ml portions of chloroform. The combined and dried (MgSO4) organic phases were evaporated in vacuo to give TLC pure 9 (710 mg, 90%). An analytical sample was recrystallized (ethyl acetate), mp 197° C. (Found: C 54.78; H 3.56; N 12.79. Calc. for $C_{10}H_8N_2O_4$: C 54.55; H 3.66; N 12.72). ¹H NMR 60 MHz (DMSO, d6) δ=2.2 (3H, s) 7–7.8 (4H, m) 11.4 (1H, broad s, exchangeable D20).

Preparation of 3-methoxy-4-(o-nitrophenyl)-5-methyisoxazole, (10) and 2, 5-dimethyl-4-(o-nitrophenyl)-3-oxo-isoxazoline, (11).

To a solution of 9 (2.25 g, 10 mmoles) in ether (60 ml) was added, with stirring, a solution of diazomethane (60 ml, 0.5M) at 0° C. Stirring was continued for 2 hours at room temperature and the remaining diazomethane was destroyed by addition of an excess of formic acid. The solution was evaporated to dryness in vacuo, and the residue was submitted to column chromatography [silica gel: 100 g; eluent: dichloromethane-ethyl acetate (90–10)] to give 860 mg (36%) of 11 and 1.35 g of 10 (57%). An analytical sample of 10 was recrystallized from Hexane to give colorless crystals, mp 72° C. (Found: C 56.45; H 4.23; N 12.11. Calc. for $C_{11}H_{10}N_2O_3$: C 56.41. H 4.30; N 11.96). 1H MNR 60 MHz (CDCl3) δ=2.35 (3H, s) 3.9 (3H, s) 7.25–7.7 (3H, m) 7.8–8.1 (1H, m). An analytical sample of 11 was recrystallized from isopropyl oxide-ethyl acetate to give yellow crystals, mp 173° C. ¹H NMR 60 MHz (CDCl3) δ=2.15 (3H,s) 3.4 (3H,s) 7.25–7.75 (3H,m) 7.8–8.1 (1H,m).

Preparation of 3-methoxy-4-(o-nitrophenyl)-5-bromomethylisoxazole (12).

A solution of 10 (0.5 g, 2.1 mmoles), NBS (0.6 g, 3.4 mmoles) and AIBN (10 mg) in CCl4 (50 ml) was stirred at 80° C. for 2 days. The suspension was filtered and the solvent evaporated to give a mixture of 10 and 12. Column chromatography on silica gel (100 g) eluting with CHCl2 gave 0.47 g (70%) of 12 as a yellow oil, 0.05 g of 10. and 0.06 g of dibromo derivative. ¹H NMR 60 MHz (CDCl3) δ=3.95 (3H, s) 4.35 (2H, s) 7.4–7.9 (3H, m) 8–8.3 (1H, m).

Preparation of 3-methoxy-4-(o-aminophenyl)-5-chloromethylisoxazole (13).

To a solution of 12 (0.3 g, 0.9 mmole) in MeOH (7ml) was added carefully a solution of $SnCl_2$ 2 $H_2O$ (0.72 g, 3.2 mmoles) in concentrated HCl (1 ml). The mixture was stirred at 80° C. for 2½ hours and the solvent was evaporated. The residue was dissolved in an ice cooled solution of sodium hydroxyde (20 ml, 10N) and extracted with CHCl2. The combined organic extracts were dried, filtered and evaporated to give TLC pure 13 (1.6 g, 95%) as a yellow oil. CC (silica gel: 30 g; eluent: $CH_2Cl_2$) afforded 13 (1.55 g, 93) a TLC pure substance. ¹H NMR 60 MHz (CDCl3) δ=3.75 (2H, broad s, exchangeable D20) 3.95 (3H, s) 4.4 (2H, s) 6.6–7.3 (4H, m). Mass spectrum, m/z −238/240 (M+).

Preparation of 3-methoxy-4-(-o-N-ethoxycarbonyl phenyl)-5-chloromethyl-isoxazole (14).

To an ice cooled solution of 13 (3.2 g, 13 mmoles) in acetone (20 ml) was added with stirring an iced solution of potassium carbonate (2.6 g, 18 mmoles) in water (30 ml) followed by addition of ethyl chloroformate (3 ml, 28 mmoles). Stirring was continued at 0° C. for 1 hour and at 25° C. for 1 hour. The mixture was extracted with three 100 ml portions of ether. The combined and dried (MgSO4) ether phases were evaporated in vacuo. The residue was purified by column chromatography (silica gel: 100 g; eluent: $CH_2Cl_2$-EtOAc (98/2)) to give pure 14 (3.1 g, 77%). An analytical sample was recrystallized (Petroleum ether) to pure 14 as colorless crystals, mp 73° C. (Found: C 54.39; H 4.95; N 9.08 calc. for $C_{14}H_{15}ClN_2O_4$: C 54.11: H 4.87; N 9.02. ¹H NMR MHz (CDCl3) δ=1.25 (3H, t, J=6 Hz) 4 (3H, s) 4.2 (2H, q, J=6 Hz) 4.4 (2H, s) 6.65 (1H, broad s) 7.1–7.6 (3H, m) 7.8–8.05 (1H, m). Mass spectrum, m/z=310/312 (M+).

Preparation of
1-methoxy-4H-5-ethoxycarbonyl-isoxazolo[5,4-c]quinoline (15)

A solution of 14 (2.76 g, 8.09 mmoles) and $K_2CO_3$ (1.23 g, 8.9 mmoles) in acetone (50 ml) was refluxed for 2 days. After evaporation to dryness in vacuo, the residue was dissolved in water (20 ml) and extracted three times with dichloromethane. The combined organic extracts were dried, filtered, and evaporated to give crude 15. Column chromatography on silica gel (50 g) eluting with Hexane/ether (60/40) gave pure 15 (2.25 g, 92%). An analytical sample was recrystallized (Petroleum ether) to give colorless crystals mp 95° C. (Found: C 61.58; H 5.30; N 10.49. Calc. for $C_{14}H_{14}O_4N_2$: C 61.31; H 5.15; N 10.11. $^1H$ NMR 60 MHz (CDCl$_3$) $\delta=1.3$ (3H, t, J=7 Hz) 4.05 (3H, s) 4.25 (2H, q, J=7 Hz) 4.95 (2H, s) 7.1–7.7 (4H, m). Mass spectrum, m/z −274 (M+).

Preparation of 1-hydroxy-dihydro-4, 5-isoxazolo-[5,4-c]quinoline Compound II

A solution of 15 (450 mg, 1.6 mmoles) in a solution of hydrogen bromide in glacial acetic acid (7 ml, 30%) was refluxed for 6 hours. After evaporation to dryness in vacuo, the residue was treated with the same reagent (7 ml) for further 5 hours. Evaporation of the reaction mixture to dryness in vacuo and recrystallization (ethyl acetate/methanol) of the residue gave Compound II (160 mg, 40%) as yellow crystals, mp 241° C. (Found: C 44.53; H 3.27; N 10.39. Calc. for $C_{10}H_9BrN_2O_2$: C 44.63; H 3.37; N 10.41). $^1H$ NMR 200 MHz (DMSO, d6) $\delta=7.68–7.77$ (2H, m) 7.82–7.88 (1H, m) 7.89–8.12 (3H, m) (2H, exchangeable D$_2$O). Mass spectrum m/z=188 (M+).

EXAMPLE 3

(Synthesis of Compound III)

Compound III was prepared according to the following scheme:

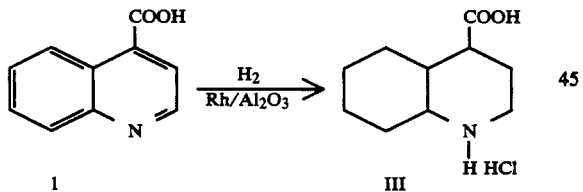

Compound III was prepared by reduction of 4-quinolinecarboxylic acid 1 to the corresponding 4-decahydroquinolinecarboxylic acid, III.

EXPERIMENTAL SECTION

A solution of 4-quinoline carboxylic acid (1.5 g., 8.6 mmoles) in acetic acid (30 ml) containing 5% Rh/Al$_2$O$_3$ (400 mg) was reduced (4.2 kg, 85° C.) in a steel bomb for 15 hours. After cooling, the catalyst was filtered and the solvent was evaporated to dryness. The residue was triturated with EtOH/Et$_2$O (50/50), filtered and washed with a minimum of Et$_2$O to give pure 4-decahydroquinoline carboxylic acid (1.4 g, 90%) as white crystals, mp >300° C., see Burckhardt, Helferick, L. Wissel, J. Prak. Chim. 39 (1966). An analytical sample of its hydrochloride salt was recrystalized in acetonitrile/water. (Found: C 54.19; H 8.62; N 6.33. Calc. for $C_{10}H_{18}ClNO_2$: C 54.66 H 8.26; N 6.38). $^1H$ NMR 400 MHz (H$_2$O) $\delta=1.3–1.5$ (4H, m) 1.67–1.76 (1H,m) 1.82–2.04 (5H, m) 2.29–2.4 (1H, m) 2.62–2.7 (1H, d t) 3.01–3.17 (1H, m) 3.46–3.57 (2H,m) 7.89 (1H, broad s, exchangeable D$_2$O) 8.29 (1H broad s, exchangeable D$_2$O).

EXAMPLE 4

(Synthesis of Compound IV)

Compound IV was prepared according to the following scheme:

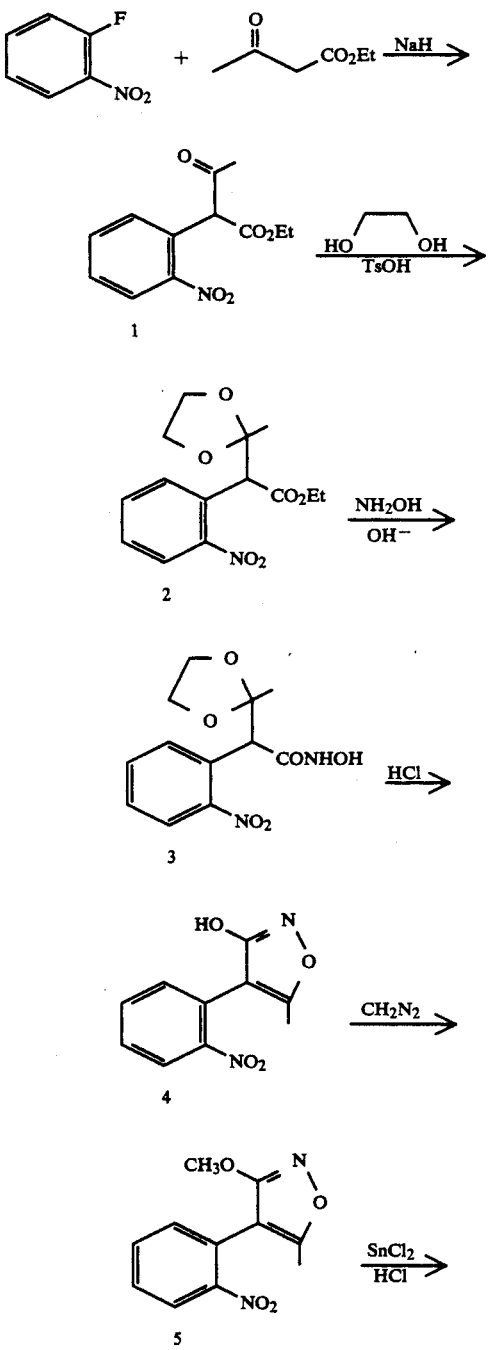

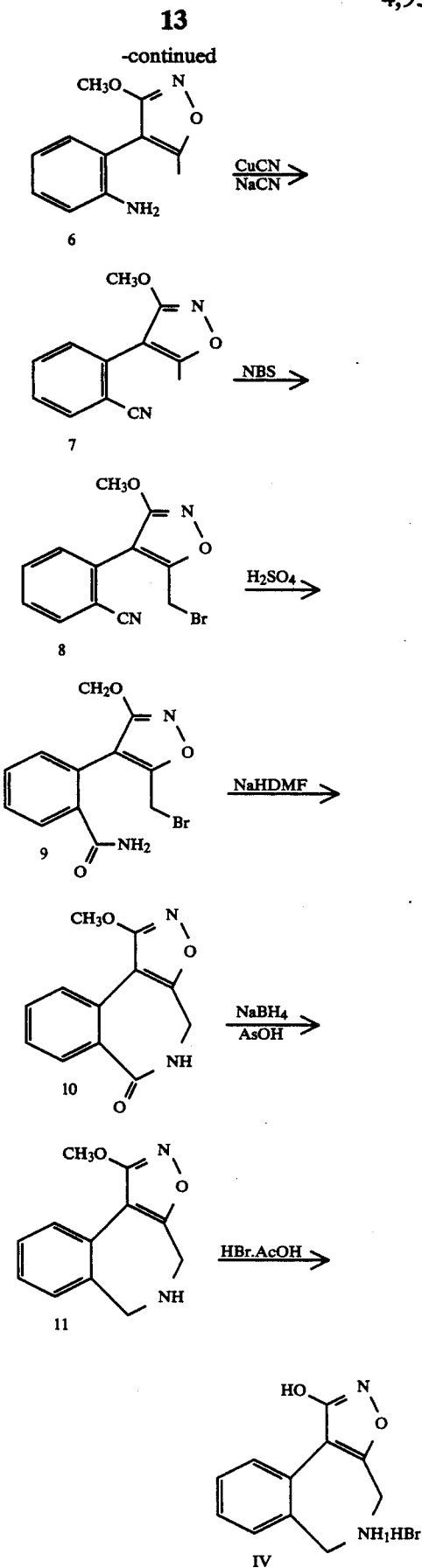

For synthesis of 1-5 see Example 2.

EXPERIMENTAL SECTION

The structure determinations of the new compounds, 5 -Compound IV were based on $^1$H NMR, Mass Spectroscopic methods and elemental analysis.

Preparation of 3-methoxy-4-(o-aniline)-5-methyl-isoxazole 6.

A solution of 5 (15.2 g, 0.065 mole) in MEOH (30 ml) was added carefully to a solution of $SnCl_2$, 2 $H_2O$ (49.7 g, 0.221 mole) in concentrated HCl (51 ml, 12N). The mixture was stirred at 70° C. for 2½ hours and the solvent was evaporated. The residue was dissolved in an ice cooled solution of sodium hydroxyde (20 ml, 10N) and extracted with $CH_2Cl_2$. The combined organic extracts were dried, filtered and evaporated to give TLC pure 6 (12.6 g, 95%) as a white solid. An analytical sample was recrystallized from isopropyl oxide to give while crystals, mp=115° C. $^1$H NMR 60 MHz (CDCl$_3$) δ=2.3 (3H, s) 3.7 (2H, broad s, exchangeable $D_2O$) 4 (3H, s) 6.6–7.2 (4H, m). Mass spectrum, m/z 204.

Preparation of 3-methoxy-4-(o-cyanobenzene)-5-methylisoxazole 7.

The amine 6 (6.3 g, 30.8 mmoles) was diazotized in a solution of sulphuric acid (9.5 ml, d=1.81) and water (12 ml) by addition of a solution of sodium nitrite (2.13 g) in water (10 ml), with crushed ice to keep the temperature at 0° C. Excess of acid was removed by addition of sodium bicarbonate (18 g) to pH 6, and the filtered solution was run into sodium cyanide solution kept at 70° C. This solution was prepared by dissolving cuprous cyanide (16.3 g) in a solution of sodium cyanide (31.6 g) in water (300 ml). After the evolution of nitrogen had ceased, the cyano compound was extracted with toluene (50 ml). The organic layer was dried (MgSO4), filtered and evaporated. The crude product was chromatographed on a silica gel column with $CH_2Cl_2$/EtOAc (98/2) and triturated with petroleum ether to give TLC pure 7 (7.25 g, 55%). An analytical sample was recrystallized from petroleum ether to give yellow crystals, mp 102° C. (Found: C 67.11; H 4.69; N 13.28. Calc. for $C_{12}H_{10}N_2O_2$: C 67.28; H 4.71; N 13.08). $^1$H NMR 60 MHz (CDCl$_3$) δ=2.4 (3H, s) 4 (3H, s) 7.3–7.8 (4H, m). Mass spectrum, m/z 214.

Preparation of 3-methoxy-4-(o-cyanobenzene)-5-bromomethylisoxazole 8.

A solution of 7 (7.25 g, 34 mmoles), NBS (9.2 g, 52 mmoles) and AIBN (40 mg) in CCl$_4$ (270 ml) was stirred at 80° C. for 10 hours. The suspension was filtered and the solvent evaporated. The crude product was chromatographed on a silica gel column with $CH_2Cl_2$/Hexane/EtOAc (65, 33, 2) as eluant to give TLC pure 8 (7.4 g, 74%) as a yellow oil. $^1$H NMR 60 MHz (CDCl$_3$) δ=4 (3H, s) 4.3 (2H, s) 7.4–7.9 (4H, m).

Preparation of 3-methoxy-4-(o-benzamide)-5-bromomethylisoxazole 9.

The cyanide 8 (7.25 g, 24.8 mmoles) was stirred in a solution of sulphuric acid (81.5 ml, d=1.81) and water (16 ml) at 90° C. for 2 hours. The mixture was poured slowly in an ice cooled solution of potassium carbonate (40 g) and extracted with $CH_2Cl_2$. The organic layers were dried, filtered and evaporated (MgSO4). The crude product was submitted to column chromatography (silica gel: 100 g; eluent:ethyl acetate) to give 6.1 g (80%) of TLC pure 9 as a white powder. An analytical sample was recrystallized (cyclohexane, benzene) to form a rubbery mass melting at 45° C. (C 46.56; H3.67; N 9.11. Calc. for $C_{12}H_{11}BrH_2O_3$: C 46.32; H 3.56; N 9). $^1$H NMR 60 MHz ($CDCl_3$) δ=3.95 (3H, s) 4.3 (2H, s) 6.1 (2H, broad s) 7.25-7.8 (4H, m). Mass spectrum m/z 310/312.

Preparation of 1-methoxy-4,5-dihydro-6H-6-=oxo-isoxazolo[5,4-d][2]- benzazepine 10.

To a suspension of NaH (565 mg, 23.5 mmoles) in dimethylformamide (52 ml) was added a solution of 9 (6.1 g, 19.6 mmoles), at 0° C., in dimethylformamide (35 ml). After 10 minutes, the reaction mixture was poured in ice cooled water and extracted with ethyl acetate. The organic layers were dried ($MgSO_4$), filtered and evaporated. The residue was triturated with ethyl acetate and filtered to give TLC pure 10 (2.25 g, 50%). An analytical sample was recrystallized from ethyl acetate, to give white crystals, mp 259° C. (Found: C 62.40; H 4.17; N 12.41. Calc. for $C_{12}H_{10}N_2O_3$: C 62.61; H 4.38; N 13.05. Calc. for $C_{12}H_{12}N_2O_2$: C 66.65; H 5.59; N 12.96). $^1$H NMR 60 MHz ($CDCl_3$) δ=3.9 (2H, s) 4.05 (3H, s) 4.2 (2H, s) 7-7.4 (3H, m) 7.8-8.05 (1H, m).

Preparation of 1-hydroxy-4,5-dihydro-6H-isoxazolo-[5,4-d][2]-benzazepine hydrobromide, Compound IV A solution of 11 (1.2 g, 5.5 mmoles) in a solution of hydrogen bromide in glacial acetic acid (40 ml, 33%) was refluxed for 10 hours. The precipitate was filtered, washed with a minimum of acetic acid and diethyl ether, and recrystallized (ethanol) to give yellow crystals (900 mg, 60%), which decompose at 230° C. (C 46.76; H 3.81; N 9.78. Calc for $C_{11}H_{11}BrN_2O_2$: C 46.76; H 3.92; N 9.89). $^1$H NMR 200 MHz (DMSO) δ=4.42 (2H, s) 4.66 (2H, s) 7.33-7.57 (3H, m) 8.04-8.09 (1H, m) 9.87 (1H, broad s, exchangeable $D_2O$) Mass spectrum m/z 202.

EXAMPLE 5

(Synthesis of Compound V)

Compound V was prepared according to the following scheme:

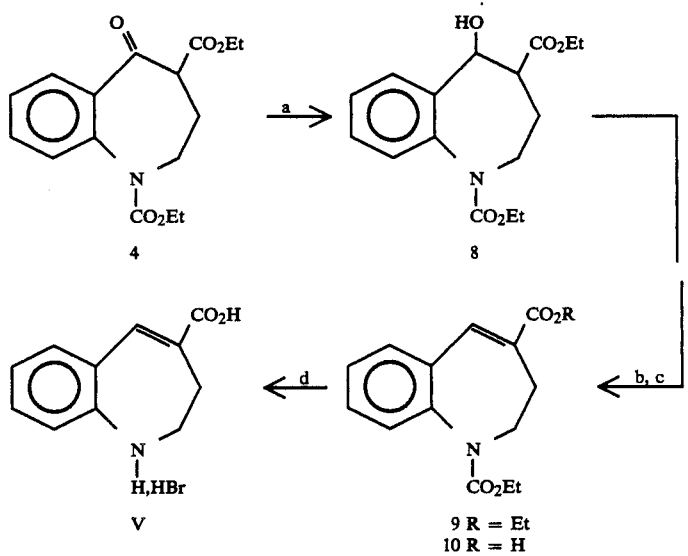

a: $NaBH_4$/MeOH; b: $H_2SO_4$/THF; c: $NaOH/H_2O$/Dioxane; HBr/AcOH.

12.17). $^1$H NMR 60 MHz ($CDCl_3$, MeOD) δ=3.7 (2H, s) 3.85 (1H s) 4.3 (3H, s). Mass spectrum m/z 230.

Preparation of 1-methoxy-4,5-dihydro-6H-isoxazolo-5,4-d][2]-benzazepine 11.

To a stirred suspension of sodium borohydride (400 mg, 10.5 mmoles) and compound 10 (500 mg, 1.28 mmoles) in dioxane (60 ml) was added acetic acid (0.625 ml, 11 mmoles) in dioxane (10 ml) at 10° C. The mixture was stirred for 15 minutes at 25° C. and heated over a period of 8 hours at 120° C. The reaction mixture was concentrated to dryness in vacuo, excess reagent was decomposed with water and extracted with chloroform. The extract was washed with water and dried over anhydrous sodium sulfate. The chloroform layer was evaporated and the residue was chromatographed on a silica gel column and eluted with $CH_2Cl_2$/MeOH (97, 3) to give 290 mg (62%) of TLC pure 11. An analytical sample was recrystallized (isopropyl oxide) to give colorless crystals, mp 128° C. (Found: C 66.50; H 5.37;

EXPERIMENTAL

For preparation of 4, see Example 6.

Preparation of N-ethoxycarbonyl-2,3,4,5-tetrahydro-4-ethoxycarbonyl-5-hydroxy-[1]-benzazepine, 8

To a solution of 4 (9 g, 29 mmoles) in MeOH (50 ml) was added at 0° C. a solution of $NaBH_4$ (0.84 g, 24 mmoles) in $H_2O$ (3.5 ml). The mixture was stirred at 0° C. for 1 hour and then poured in water (100 ml) and extracted with $CH_2Cl_2$. The organic layers were dried ($MgSO_4$), filtered and evaporated. The residue was chromatographed [silica gel: 100 g, eluent EtOAc/hexane (40/60)] to give pure 8 as a white solid (8.2 g, 90%). An analytical sample was recrystallized from hexane, mp 93° C. (Found: C; H; N . Calc. for $C_{16}H_{21}NO_5$: C 62.53; H 6.89; N 4.56). 1H NMR ($CDCl_3$) δ=0.9-1.5

(6H, 2 overlapped t) 1.6–3.5 (4H, m, one exchangeable D$_2$O ) 3.8–4.3 (4H, 2 overlapped q) 4.9–5.2 (1H, m) 7–7.4 (4H, m). IR (CCl$_4$) 3400 (w, large signal) 2980 (m) 2940 (w) 1705 (s) 1610 (w) 1490 (m) 1460 (m) 140 (m) 1410 (m) 1385 (m) 1310 (s). Mass spectrum m/z 307.

Preparation of N-ethoxycarbonyl-2,3-dihydro-4-ethoxycarbonyl-[1]-benzazepine 9.

Compound 8 (7 g, 22.8 mmoles) was dissolved in THF (100 ml) and refluxed in presence of H$_2$SO$_4$ (13 ml) for 2 hours. THF was evaporated and the residue was poured in ice cooled water, extracted with ether (100 ml). The organic layer was dried (MgSO$_4$), and evaporated. The residue was chromatographed (silica gel: 120 g, eluent: CH$_2$Cl$_2$/EtOAc (95/5)] to give a viscous liquid 9 (5.7 g, 87%). (Found: C; H; N . Calc. for C$_{16}$H$_{19}$NO$_4$: C 66.42; H 6.62; N 4.84). 1H NMR (CDCl$_3$) δ=1.1–1.5 (6H, 2 overlapped t, J=7 Hz) 2.9 (2H, t) 3.6 (2H, t) 3.9–4.4 (4H, 2 overlapped q, J=7 Hz) 7–7.5 (4H, m) 7.5–7.7 (1H, m) IR (CCl$_4$) 2990 (m) 2950–2870 (several bands, ) 1705 (s) 1635 (m) 1605 (w) 1495 (m) 1470 (w) 1450(m) 1410 (s) 1390 (s) 1370 (m) 1340 (w) 1320 (s). Mass spectrum m/z 289.

Preparation of N-ethoxycarbonyl-2,3-dihydro-(1]-benzazepine-4-carboxylic acid 10

Compound 9 (5 g, 17.2 mmoles) was dissolved in dioxane (11.5 ml) and a solution of sodium hydroxyde (11.5 ml, 1.5M) was added. The mixture was heated for 2 hours and poured in ice cooled water. The aqueous layer was extracted at pH 12 with Et$_2$O (50 ml), acidified to pH 2 and reextrated with EtOAc (100 ml). This layer was dried (MgSO$_4$), filtered and evaporated to give yellow crystals (4.2 g, 90%), after recrystallization (cyclohexane/CCl$_4$) mp 176° C. $^1$H NMR (CDCl$_3$) δ=1.25 (3H, t, J=7 Hz) 2.9 (2H, t) 3.5–3.9 (2H, m) 4.2 (2H, q, J=7 Hz) 7–7.6 (4H, m) 7.8 (1H, s). IR (CCl$_4$) 3500–3000 (large signal) 3000 (w) 1695 (s) 1630 (w) 1600 (w) 1575 (w) 1490 (w) 1450 (w) 1410 (m) 1385 (w) 1370 (2) 1340 (w) 1320 (m). Mass spectrum m/z 261.

Preparation of dihydro-1,2-3H-[1]-benzazepine-4-carboxylic acid hydrobromide Compound V Compound 10 (2 g, 7.66 mmoles) was dissolved in a solution of hydrogen bromide in glacial acetic acid (40 ml, 33%) and refluxed for 18 hours. The precipitate was filtered, washed with acetic acid and ether, recrystallized (H$_2$O, CH$_3$CN) to give a yellow powder (1.25 g, 60%) mp >260° C. (Calc. for C$_{11}$H$_{12}$NO$_2$Br. C 48.91; H 4.48; N 5.19). (Found C 49.09 H 4.49 N 5.16) $^1$H NMR 200 MHz (DMSO) 2.74 (2H, broad s) 3.24 (2H, broad s) 6.64–6.89 (2H, m) 7.04–7.17 (1H, m) 7.24 (1H, dd, J=7 Hz) 7.52 (1H, s) 12–13 (broad s). Mass spectrum m/z 189.

EXAMPLE 6

(Synthesis of Compound VI)

Compound VI was prepared according to the following scheme:

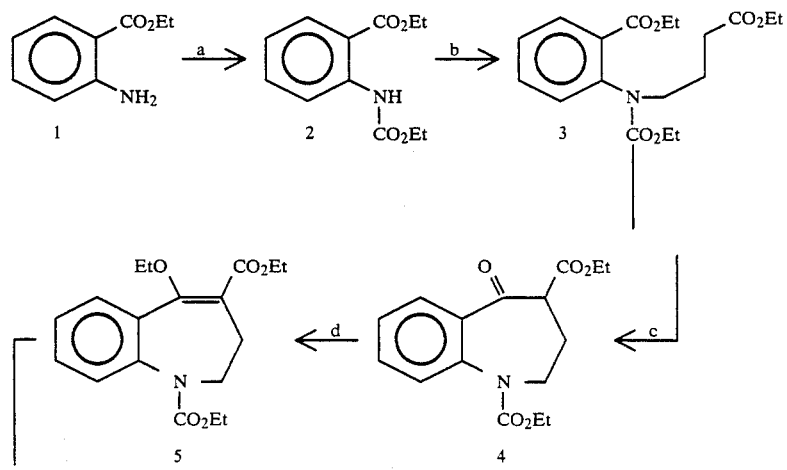

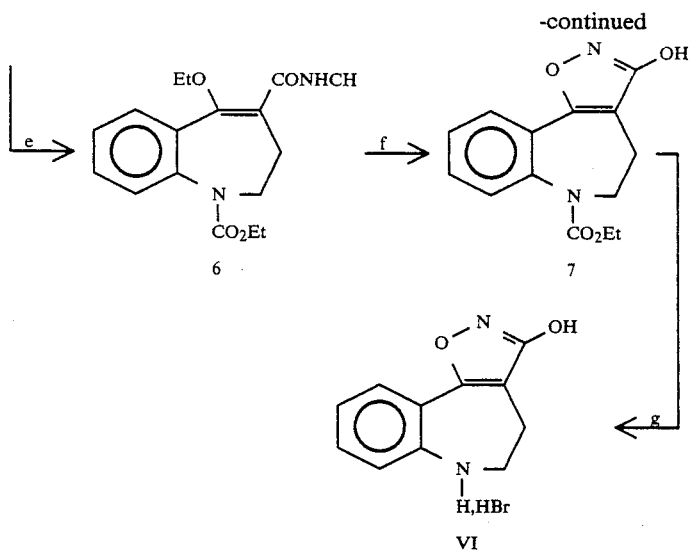

a: ClCO₃Et/K₂CO₃/Acetone; b: Br(CH₂)₃CO₂Et/NaH/DMF; c: NaOEt benzene;
d: CH(OEt)₃/Amberlyst 15; e: NH₂OH, HCl/KOH/MeOH; f: HCl/MeOH; g: HBr, AcOH.

EXPERIMENTAL SECTION

Preparation of Ethyl-N-ethoxycarbonyl-o-aminobenzoate 2

To an ice cooled solution of ethyl-o-aminobenzoate 1 (33 g, 0.2 mole) in acetone (270 ml) was added with stirring an ice cooled solution of potassium carbonate (36.7 g, 0.27 mole) in water (214 ml) followed by addition of ethyl chloroformate (43 g, 0.4 mole). Stirring was continued at 0° C. for 1½ hour and at 25° C. for 2 hours. The mixture was poured in water (300 ml) and extracted with three 300 ml portions of ether. The combined and dried (MgSO₄) ether phases were evaporated in vacuo to give pure 2 (46.7 g, 98%). The product was recrystallized (EtOH, H₂O) to give colorless crystals, mp <40° C. (Calc. for $C_{12}H_{15}NO_4$: C 60.75; H 6.37; N 5.90). (Found C 60.75; H 6.29; N 5.85) ¹H NMR (CDCl₃) δ=1.3 (3H, t, J=7 Hz) 1.4 (3H, t, J=7 Hz) 4.2 (2H, q, J=7 Hz) 4.3 (2H, q, J=7 Hz) 6.9–8.5 (4H, AA'BB'). IR (CCl₄): 3300(m), 2980(m), 1735(s), 1690(s), 1600(s), 1510(w), 1450(s).

Preparation of Ethyl-N-ethoxycarbonyl-N-(ethylbutrate)-o-aminobenzoate 3

To a suspension of NaH (3.86 g, 0.161 mole) in DMF (30 ml) was added dropwise a solution of 2 (34.7 g, 0.146 mole) in DMF (100 ml) followed by addition of a solution of ethylbromobutyrate (28.7 g, 0.146 mole) in DMF (25ml) over 2 hours to maintain the temperature at 35° C. Stirring was continued for 6 hours at this temperature; The mixture was poured in ice cooled water (300 ml) and extracted with three 200 ml portions of ether; The combined and dried (MgSO₄) ether phases were evaporated in vacuo. The residue was purified by column chromatography [Silica gel: 400 g; eluent: EtOAc/Hexane (10/90) and (50/50)] to give pure 3 (31 g, 60%) as a colorless viscous liquid. (Calc. for $C_{18}H_{25}NO_6$: C 61.52; H 7.17; N 3.99 Found C 61.15; H 4.05; N 7.11). ¹H NMR 200 MHz(CDCl₃) δ=1.08 (3H, t, J=7.5 Hz) 1.22 (3H, t, J=7.5 Hz) 1.38 (3H, t, J=7.5 Hz) 1.94 (2H, m) 2.36 (2H, m) 3.45 (1H, m) 3.85 (1H, m) 4.05 (2H, q, J=7.5 Hz) 4.10 (2H, q, J=7.5 Hz) 4.31 (2H, q, J=7.5 Hz) 7.21–7.57 (3H, m) 7.96 (1H, dd, J=7H). IR (CCl₄) 2990 (m) 1735 (s) 1710 (s) 1610 (w) 1490 (w) 1450 (m). Mass spectrum m/z 351.

Preparation of N-Ethoxycarbonyl-2,3-dihydro-4H-4-ethoxycarbonyl-5-oxo-[1]-benzazepine 4

To a suspension of NaH (2.36 g, 98 mmoles) in N-methyl-2-pyrolidone (33 ml) was added dropwise a solution of 3 (24.7 g), 70 mmoles) in N-methyl-pyrolidone (33 ml). After one and one half hours, the reaction mixture was poured in ice cooled water (100 ml) and extracted with EtOAc. The organic layers were dried (MgSO₄), filtered and evaporated to give pure 4 (18 g, 85%) as a colorless, viscous liquid, (Calc. for $C_{16}H_{19}NO_5$: C 62.94; H 6.27; N 4.59 Found C 62.83; H 6.45; N 4.62) ¹H NMR 200 MHz (CDCl₃) δ=1.12 (3H, t, J=7.5 Hz) 1.28 (3H, 2 overlapped t, J=7.5 Hz) 2.42 (2H, m) 3.59 (1H, m) 3.84 (1H, t) 4–4.3 (a total of 5 H, 2 overlapped q, J=7.5 Hz, overlapped by a t) 7.1–7.87 (4H, m) 12.66 (0.45H, s). IR (CCl₄) 2990 (m) 2940 (w) 1705 (s) 1610 (w) 1410 (m) 1385 (m) 1310 (s) 1180 (m). Mass spectrum a/z 305.

Preparation of N-ethoxycarbonyl-2,3-dihydro-4-ethoxycarbonyl-5-ethoxy-[1]-benzazepine 5

A solution of 4 (7.13 g, 23 mmoles), triethylorthoformate (19.4 ml, 13 mmoles) and Amberlyst 15 (2.33 g) was stirred at 130° C. The ethanol was removed by distillation and the reaction was heated at 180° C. for 4 hours. After cooling, ethyl acetate (100 ml) was added. The solution was filtered, the filtrate evaporated and the product was chromatographed [Silica gel: 120 g, eluent: CH₂Cl₂/EtOAC (95/5)], and recrystallyzed from petroleum ether to give white crystals (7 g, 90%) mp 60° C. (Found: C 64.98; H 7.06; N 4.16. Calc. for $C_{18}H_{23}NO_5$: C 64.85; H 6.95; N 4.20). 1H NMR (CDCl₃) δ=0.95–1.55 (9H, 3 overlapped t) 2.26 (2H, broad s) 3.5–4.5 (8H, m) 7.1–7.5 (4H, m). IR (CCl₄) 2990 (m) 2940 (w) 1710 (s) 1625 (w) 1490 (w) 1450 (w) 1410 (m) 1380 (m) 1330 (s) 1235 (m). Mass spectrum m/z 333.

Preparation of n-ethoxycarbonyl-2,3-dihydro-4-N-hydroxycarboxamide-5-ethoxy-[1]-benzazepine 6

To a stirred solution of potassium hydroxyde (5.4 g, 96 mmoles) in methanol (14 ml) was added at 0° C. a solution of hydroxylamine hydrochloride (5.3 g, 76 mmoles)in methanol (19 ml). After stirring for further 90 minutes at 0° C. a solution of 5 (6.3 g, 19 mmoles) was added and the solution was allowed to stand at 4° C. for 48 hours. Upon addition of glacial acetic acid (11 ml) the mixture was filtered. The filtrate was evaporated in vacuo and the residue was recrystallized from EtOAc to obtain a pink powder (3 g, 50%) mp 160° C. (Found: C 60.22; H 6.28; N 8.86. Calc. for $C_{16}H_{20}N_2O_5$: C 59.99; H 6.29; N 8.74). 1H NMR (CDCl$_3$) δ=0.8–1.5 (6H, m) 2–2.7 (2H, broad s) 3.5–4.3 (6H, m) 7.3 (4H, s) 10 (2H, broad s, exchangeable D$_2$O ). IR (CHCl$_3$) 3400–2980 (broad signal) 1695 (s) 1640 (s) 1485 (w) 1405 (m) 1385 (m) 1330 (m) 1140 (w) 1110 (w). Mass spectrum m/z 320.

Preparation of 3-hydroxy-4,5-dihydro-6-ethoxycarbonyl-[5,4-d]-isoxazolo-[1]-benzazepine 7

(2.43 g, 7.6 mmoles) was dissolved in a methanolic solution of hydrogen chloride (30 ml, 50%) which was refluxed for 3 hours. The solution was poured in ice cooled water (50 ml) and extracted with methylene chloride. The organic layers were dried (MgSO$_4$) and evaporated and the residue was recrystallized from EtOAc to give a white powder (1.83 g, 88%) mp 258° C. (Found: C 61.56; H 5.21; N 10.29. Calc. for $C_{14}H_{14}N_2O_4$ C 61.31; H 5.15; N 10.21). 1H NMR (CDCl$_3$-MeOD) δ=1.1 (3H, t, J=7 Hz) 2.4–3 (2H, m) 3–3.3 (1H, m) 3.8–4.4 (3H, m) 7.2–7.5 (3H, m) 7.6–7.9 (1H, m). Mass spectrum m/z 274.

Preparation of 3-hydroxy-4,5-dihydro-6H-[5,4-d]-isoxazo-[1]-benzazepine hydrobromide, Compound VI Compound 7 (1.5 g, 5.4 mmoles) was dissolved in a solution of hydrogen bromide in glacial acetic acid (23 ml, 33%) and refluxed for hours. The brown precipitate was filtered, washed with acetic acid and ether, and recrystallized from ethanol to give colorless crystals (0.8 g, 50%) mp 218° C. (Found: C 46.54; H 3.94; N 9.87. Calc. for $C_{11}H_{11}N_2O_2Br$: C 46.66; H 3.92: N 9.90). 1H NMR 200 MHz (DMSO) δ=2.56 (3H, t, J=5 Hz) 3.24 (3H, t, J=5 Hz) 6.80–6.95 (2HY, m) 7.12–7.20 (1H, m) 7.66–7.71 (1H, m). Mass Spectrum m/z 202.

EXAMPLE 7

(Synthesis of Compound VII)

Compound VII was prepared according to the following scheme:

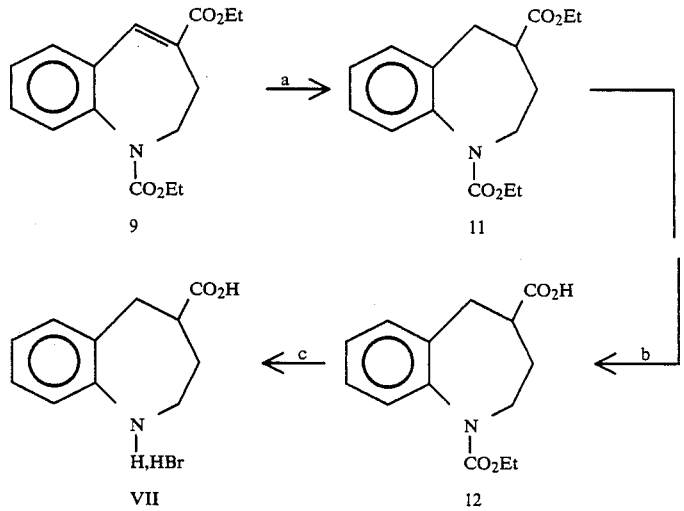

a: $H_2/PtO_2/9$ Atm.; b: NaOH/H$_2$O/dioxane; c: HBr/AcOH

EXPERIMENTAL

See Example 5 for synthesis of 9

Preparation of N-ethoxycarbonyl-1,2,3,4-tetrahydro-5-ethoxycarbonyl- 6H-[1]-benzazepine 11

A solution of 9 (5.5 g, 19 mmoles) in EtOH (55 ml) containing PtO$_2$ (300 mg) was reduced (9 Atm, 25° C.) in a steel bomb for 10 hours. The catalyst was filtered and the solvent was evaporated to dryness. The residue was chromatographed [Silica gel: 120 g; eluent CHCH$_2$Cl$_3$/EtOAc (95/5)] to give pure 11 (4.3 g, 80%) mp 60° C. (Calc. for $C_{16}H_{21}NO_4$: C 65.96; H 7.27; N 4.81 Found C 65.76; H 7.55; N 4.82) $^1$H NMR (CDCl$_3$) δ=1.2 (6H, 2 overlapped t, J=7 Hz) 1.8–2.2 (2H, m) 2.3–2.7 (1H, m) 2.8–3.05 (2H, m) 3.2–3.7 (1H, m) 3.8–4.3 (5H, 2 overlapped q, J=7 Hz) 7.1 (4H, s). IR (CHCl$_3$) 2980 (m) 2930 (m) 1725 (s) 1690 (s) 1610 (w) 1590 (w) 1490 (w) 1440 (w) 1410 (w) 1385 (w) 1310 (m). Mass spectrum m/z 291.

Preparation of N-ethoxycarbonyl-1,2,3,4-tetrahydro-6H[1]-benzazepine- 5-carboxylic acid 12

Compound 12 was obtained from 11 in 99% yield. (See Example 5 for preparation of 10 and Compound V) It is a white solid, recrystallized from CCl$_4$/cyclohexane, mp 102° C. (Calc. for $C_{14}H_{17}NO_4$: C 63.87; H 6.51; N 5.32 Found C 62.71; H 6.53; N 5.42). $^1$H NMR (CDCl$_3$) 0.9–1.4 (3H, m) 1.8–2.3 (2H, m) 2.3–2.8 (1H, broad s) 2.8–3.2 (2H, m) 3.2–3.8 (1H, broad s) 3.8–4.4 (3H, m) 9.1 (1H, broad s, exchangeable D$_2$O ). IR (CHCl$_3$) 3000–2800 (large band) 2980 (m) 1690 (s) 1610 (w) 1585 (w) 1490–1410 (several bands) 1310 (s). Mass spectrum m/z 263.

Preparation of 1,2,3,3-tetrahydro-5H-[1]-benzazepine-4-carboxylic acid, Compound VII.

Compound VII was obtained from 12 in 60% yield. It is a white powder, recrystallized from H$_2$O/CH$_3$CN, mp 212° C. (Calc. for C$_{11}$H$_{14}$NO$_2$Br: C 48.55; H 5.19; N 5.15 Found C 48.68; H 5.17; N 5.20) $^1$H NMR 200 MHz (DMSO) 2.12–2.32 (2H, m) 2.57–2.77 (1H, broad s) 3.12–3.55 (3H, m) 3.45–3.62 (1H, m) 7.27–7.52 (4H, m) 8.5–10 (2H, broad s, exchangeable D$_2$O ). Mass spectrum m/z 191.

The compounds of the present invention exhibit characteristics similar to GABA in that the compounds serve to protect the cornea through maintenance of the endothelial fluid pump. The compounds have also been shown to induce deturgescence of the cornea.

The compounds can be used alone or in combination in physiologically compatible solutions having a pH of about 6.8–8.0 and an osmolality of between about 250 and 350 mOsm/Kg. For example, the compounds can be used in combination with a balanced salt solution such as the solution available from Alcon Laboratories, Inc. as BSS ®. The compounds can also be used in combination with solutions containing dextrose, glutathione, bicarbonate and/or other tissue maintenance factors, such as the solution sold by Alcon Laboratories, Inc. as BSS Plus ®. In addition the compounds can be substituted for glutathione in solutions containing glutathione.

The concentration of the compounds in such compositions will vary depending on factors such as the relative activity of the compound or compounds utilized, the presence or absence of other tissue maintenance factors (e.g., dextrose) in the compositions, and various clinical factors such as the type of surgery in which the compositions will be employed. The compounds will typically be utilized in a concentration of between about 0.001 to 1.0 mM, preferably about 0.001 mM.

The following Examples 8–10 further illustrate the use of the compounds of the present invention in tissue irrigating compositions, and the effectiveness of the compounds in reducing corneal swelling.

EXAMPLE 8

An aqueous irrigating solution of the following composition was prepared and tested for its pharmacological efficacy.

| Component | Concentration (mM) |
|---|---|
| NaCl | 111.56 |
| Kcl | 4.82 |
| CaCl$_2$.2H$_2$O | 1.04 |
| MgCl$_2$.6H$_2$O | 0.78 |
| NaH$_2$PO$_4$.2H$_2$O | 0.66 |
| NaHCO$_3$ | 29.17 |
| Dextrose | 5.01 |
| Compound I | 0.01 |
| Osmolality | 292 mOsm/Kg |
| pH | 7.0 +/− 0.1 |

A reference solution was made containing the components set forth above with 0.01 mM GABA substituted for Compound I.

Paired bovine eyes were obtained and kept in moist chambers maintained at 4° C. until dissection. The epithelium was scraped off and the corneas excised. The corneas were mounted in water jacketed perfusion cells with both endothelial and epithelial sides covered with the perfusion solution.

The mounted corneas were kept at 4° C. for two hours to obtain a corneal swelling of about 200 microns. At the end of this period, the corneas were mounted in the perfusion chamber and endothelial perfusions were begun at 37° C. at 200 microliters per minute. The epithelial chamber solution was discarded and substituted with medical silicone oil.

One cornea of each pair was perfused with a solution of the composition set forth above, whereas the other cornea was used as a reference and perfused with a solution identical to the solution set forth above, except for the substitution of GABA for Compound I.

Perfusion continued for 8 hours.

Corneal thicknesses were measured immediately after the cornea was mounted ("Time 0") and at ½ hour intervals during the 8 hour perfusion period using a Haag Streit Slit Lamp (Model 900) equipped with a pachometer. Thickness differences were calculated for each cornea by subtracting the thickness read each time from the initial thickness at Time 0. The mean thickness difference for each solution at each time was then calculated and expressed in micrometers +/−SEM. The differences obtained for both solutions at each time were compared by a Student "t" test (p=0.05).

The thickness evolution of the 5 paired corneas perfused either with Compound I or GABA are summarized in Tables 1, 2 , 3, and 4 below. Individual thicknesses are listed in Tables 1 and 3 and individual thickness differences as well as mean thickness differences in Tables 2 and 4. Corneas perfused with Compound I started to deturgesce one hour after the beginning of the perfusion. The thickness decrease was regular for 6 hours and reduced thereafter. A maximum thickness decrease of 77.0+/−10.2 micrometers was measured after 8 hours of perfusion (FIG. 1). The paired corneas perfused with GABA swelled for one hour (10.8 micrometers) and then deturgesced over the entire perfusion. The rate of deturgescence was similar to that of Compound I for five hours but slowed down thereafter. A maximum thickness decrease of 70.0+/−5.6 was measured after 8 hours of perfusion (FIG. 1).

The data demonstrated that the thickness decrease was always higher for corneas perfused with Compound I than the paired corneas perfused with GABA. Moreover, GABA induced a slight initial swelling whereas Compound I did not produce such an effect. However, no significant statistical difference (P=0.05) was found between both curves.

At the end of the perfusion period the endothelium of each cornea was covered for 1.5 minutes with a Trypan blue staining solution (Trypan blue 250 milligram % in NaCl 0.9%). The corneas were then rinsed with 0.9% NaCl and their integrity was evaluated using the following scoring system.

+++ normal endothelium without any damage

++ more than ¾ of the endothelium without any damage

+ between ¾ and ½ of the endothelium without damage 0 less than ½ of the endothelium without damage Only pairs with corneas "+++" or "++" were retained for calculation. The scoring for each cornea is indicated in Tables 1 and 3.

TABLE 1

COMPOUND I
Corneal Thickness (μm)

| Time (hours) | Cornea 1 | 2 | 3 | 4 | 5 |
|---|---|---|---|---|---|
| 0.0 | 903 | 890 | 953 | 840 | 833 |
| 0.5 | 917 | 910 | 940 | 830 | 820 |
| 1.0 | 900 | 900 | 943 | 817 | 830 |
| 1.5 | 900 | 897 | 923 | 803 | 830 |
| 2.0 | 900 | 890 | 930 | 800 | 810 |
| 2.5 | 890 | 880 | 920 | 800 | 810 |
| 3.0 | 880 | 873 | 910 | 783 | 800 |
| 3.5 | 883 | 863 | 907 | 787 | 793 |
| 4.0 | 873 | 867 | 887 | 780 | 780 |
| 4.5 | 873 | 853 | 890 | 773 | 767 |
| 5.0 | 873 | 843 | 887 | 770 | 770 |
| 5.5 | 870 | 843 | 880 | 767 | 760 |
| 6.0 | 850 | 840 | 880 | 743 | 750 |
| 6.5 | 853 | 837 | 867 | 750 | 747 |
| 7.0 | 863 | 840 | 867 | 767 | 743 |
| 7.5 | 850 | 830 | 867 | 767 | 740 |
| 8.0 | 857 | 827 | 860 | 760 | 730 |
| Histo | +++ | +++ | ++ | +++ | +++ |

TABLE 2

COMPOUND I
Corneal Thickness Difference (μm)

| Time (hours) | Cornea 1 | 2 | 3 | 4 | 5 | Mean +/− | SEM |
|---|---|---|---|---|---|---|---|
| 0.0 | 0 | 0 | 0 | 0 | 0 | 0.0 | 0.0 |
| 0.5 | 14 | 20 | −13 | −10 | −13 | −0.4 | 7.2 |
| 1.0 | −3 | 10 | −10 | −23 | −3 | −5.8 | 5.4 |
| 1.5 | −3 | 7 | −30 | −37 | −3 | −13.2 | 8.6 |
| 2.0 | −3 | 0 | −23 | −40 | −23 | −17.8 | 7.4 |
| 2.5 | −13 | −10 | −33 | −40 | −23 | −23.8 | 5.7 |
| 3.0 | −23 | −17 | −43 | −57 | −33 | −34.6 | 7.1 |
| 3.5 | −20 | −27 | −46 | −53 | −40 | −37.2 | 6.1 |
| 4.0 | −30 | −23 | −66 | −60 | −53 | −46.4 | 8.5 |
| 4.5 | −30 | −37 | −63 | −67 | −66 | −52.6 | 7.9 |
| 5.0 | −30 | −47 | −66 | −70 | −63 | −55.2 | 7.4 |
| 5.5 | −33 | −47 | −73 | −73 | −73 | −59.8 | 8.4 |
| 6.0 | −53 | −50 | −73 | −97 | −83 | −71.2 | 8.9 |
| 6.5 | −50 | −53 | −86 | −90 | −86 | −73.0 | 8.8 |
| 7.0 | −40 | −50 | −86 | −73 | −90 | −67.8 | 9.9 |
| 7.5 | −53 | −60 | −86 | −73 | −93 | −73.0 | 7.5 |
| 8.0 | −46 | −63 | −93 | −80 | −103 | −77.0 | 10.2 |

TABLE 3

GABA
Corneal Thickness (μm)

| Time (hours) | Cornea 1 | 2 | 3 | 4 | 5 |
|---|---|---|---|---|---|
| 0.0 | 917 | 903 | 900 | 813 | 820 |
| 0.5 | 920 | 907 | 920 | 823 | 820 |
| 1.0 | 930 | 920 | 893 | 837 | 827 |
| 1.5 | 930 | 900 | 897 | 823 | 823 |
| 2.0 | 930 | 883 | 887 | 820 | 820 |
| 2.5 | 927 | 880 | 890 | 820 | 800 |
| 3.0 | 910 | 877 | 873 | 807 | 800 |
| 3.5 | 900 | 873 | 863 | 803 | 770 |
| 4.0 | 887 | 867 | 867 | 790 | 763 |
| 4.5 | 887 | 860 | 853 | 787 | 760 |
| 5.0 | 887 | 863 | 857 | 770 | 737 |
| 5.5 | 883 | 860 | 833 | 767 | 737 |
| 6.0 | 877 | 853 | 830 | 757 | 737 |
| 6.5 | 870 | 857 | 833 | 757 | 733 |
| 7.0 | 877 | 843 | 830 | 757 | 730 |
| 7.5 | 867 | 853 | 823 | 750 | 740 |
| 8.0 | 863 | 843 | 817 | 740 | 740 |
| Histo | +++ | ++ | +++ | +++ | +++ |

TABLE 4

GABA
Corneal Thickness Difference (μm)

| Time (hours) | Cornea 1 | 2 | 3 | 4 | 5 | Mean +/− | SEM |
|---|---|---|---|---|---|---|---|
| 0.0 | 0 | 0 | 0 | 0 | 0 | 0.0 | 0.0 |
| 0.5 | 3 | 4 | 20 | 10 | 0 | 7.4 | 3.5 |
| 1.0 | 13 | 17 | −7 | 24 | 7 | 10.8 | 5.2 |
| 1.5 | 13 | −3 | −3 | 10 | 3 | 4.0 | 3.3 |
| 2.0 | 13 | −20 | −13 | 7 | 0 | −2.6 | 6.1 |
| 2.5 | 10 | −23 | −10 | 7 | −20 | −7.2 | 6.8 |
| 3.0 | −7 | −26 | −27 | −6 | −20 | −17.2 | 4.5 |
| 3.5 | −17 | −30 | −37 | −10 | −50 | −28.8 | 7.1 |
| 4.0 | −30 | −36 | −33 | −23 | −57 | −35.8 | 5.7 |
| 4.5 | −30 | −43 | −47 | −26 | −60 | −41.2 | 6.1 |
| 5.0 | −30 | −40 | −43 | −43 | −83 | −47.8 | 9.1 |
| 5.5 | −34 | −43 | −67 | −46 | −83 | −54.6 | 8.9 |
| 6.0 | −40 | −50 | −70 | −56 | −83 | −59.8 | 7.6 |
| 6.5 | −47 | −46 | −67 | −56 | −87 | −60.6 | 7.6 |
| 7.0 | −40 | −60 | −70 | −56 | −90 | −63.2 | 8.3 |
| 7.5 | −50 | −50 | −77 | −63 | −80 | −64.0 | 6.4 |
| 8.0 | −54 | −60 | −83 | −73 | −80 | −70.0 | 5.6 |

EXAMPLE 9

The following formulation illustrates an aqueous irrigating solution in accordance with the present invention. The formulations may contain one or more of Compounds I-VII.

| Component | Concentration (mM) |
|---|---|
| Compound(s) I-VII | 0.001-1 |
| Sodium Chloride | 109.5 |
| Potassium Chloride | 10.1 |
| Calcium Chloride | 4.3 |
| Magnesium Chloride | 1.5 |
| Sodium Acetate | 28.6 |
| Sodium Citrate | 5.78 |
| Sterile $H_2O$ | q.s |
| pH | 7.4 |
| Osmolality (mOsm/Kg) | 300 |

EXAMPLE 10

The following formulation represents a further illustration of an aqueous irrigating solution according to the present invention

| Components | Concentrations (mM) |
|---|---|
| Compound(s) I-VII | 0.001-1 |
| Sodium Chloride | 122.2 |
| Potassium Chloride | 5.08 |
| Disodium Phosphate | 3.0 |
| Sodium Bicarbonate | 25.0 |
| Calcium Chloride | 1.05 |
| Magnesium Chloride | 0.98 |
| Dextrose | 5.01 |
| Glutathione Disulfide | 0.30 |
| Sterile $H_2O$ | q.s |
| pH | 7.4 |
| Osmolality (mOsm/Kg) | 305 |

What is claimed is:

1. A compound selected from the group consisting of:

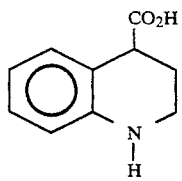

and

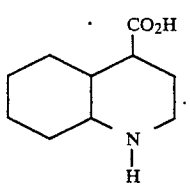

2. A compound of the formula:

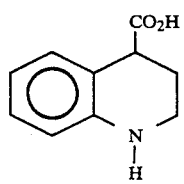

3. An aqueous irrigating solution comprising a therapeutically effective amount of a compound selected from the group consisting of:

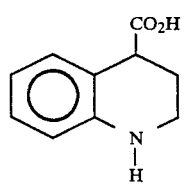

and

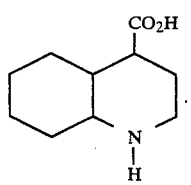

4. A solution according to claim 3 wherein the compound is contained in the solution in an amount of between about 0.001 to 1 mM.

5. An aqueous irrigating solution according to claim 3, wherein the solution comprises: 109.5 mM sodium chloride, 10.1 mM potassium chloride, 4.3 mM calcium chloride, 1.5 mM magnesium chloride, 28.6 mM sodium arcetate, 5.78 mM sodium citrate and about 0.001-1 mM of the compound.

6. An aqueous irrigating solution wherein the solution comprises: 109.5 mM sodium chloride, 10.1 mM potassium chloride, 4.3 mM calcium chloride, 1.5 mM magnesium chloride, 28.6 mM sodium acetate, 5.78 mM sodium citrate and a therapeutically effective amount of a compound of the formula:

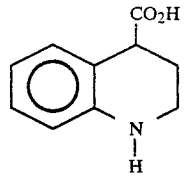

7. An irrigating solution according to claim 3 wherein the solution comprises: between about 130 and 180 mM sodium ions, between about 3 and 10 mM potassium ions, between about 1 and 5 mM calcium ions, between about 0.5 and 7 mM magnesium ions, between about 10 and 50 mM bicarbonate ions, between about 2 and 10 mM dextrose, and between about 0.03 and 0.5 mM oxidized glutathione or the equivalent amount of reduced glutathione, wherein the solution has a pH of between about 6.8 and 8.0 and an osmolality of between 150 and 350 mOsm/kg.

8. An aqueous irrigating solution wherein the solution comprises: between about 130 and 180 mM sodium ions, between about 3 and 10 mM potassium ions, between about 1 and 5 mM calcium ions, between about 0.5 and 7 mM magnesium ions, between about 10 and 50 mM bicarbonate ions, between about 2 and 10 mM: dextrose, and between about 0.03 and 0.05 mM oxidized glutathione or the equivalent amount of reduced glutathione and a therapeutically effective amount of a compound of the formula:

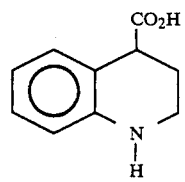

wherein the solution has a pH of between about 6.8 and 8.0 and an osmolality of between 150 and 350 mOsm/kg.

9. A method of maintaining tissue stability during surgery comprising: applying an irrigating solution according to claim 3 to the affected tissue.

10. A method of maintaining tissue stability during surgery comprising a compound of the structure:

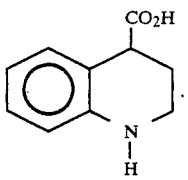

11. A method of irrigating ocular tissue to prevent or reduce corneal swelling during ophthalmic surgery, comprising: topically applying an irrigating solution according to claim 3 to the affected tissue.

12. A method of irrigating ocular tissue to prevent or reduce corneal swelling during ophthalmic surgery, comprising: topically applying an irrigating solution according to claim 6 to the affected tissue.

13. The solution of claim 6 wherein the compound concentration is between about 0.001 to 1.0 mM.

14. The solution of claim 8 wherein the compound concentration is between about 0.001 to 1.0 mM.

15. The method of claim 12 wherein the compound concentration is between about 0.001 to 1.0 mM.

* * * * *